United States Patent
Gonda

(10) Patent No.: US 9,372,198 B2
(45) Date of Patent: *Jun. 21, 2016

(54) DIAGNOSIS OF ENTRY OF GASTROINTESTINAL CONTENTS INTO RESPIRATORY TRACT OF HUMANS AND ANIMALS

(75) Inventor: Igor Gonda, San Francisco, CA (US)

(73) Assignees: ARADIGM CORPORATION, Hayward, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 63 days.

This patent is subject to a terminal disclaimer.

(21) Appl. No.: 13/162,344

(22) Filed: Jun. 16, 2011

(65) Prior Publication Data

US 2011/0312017 A1    Dec. 22, 2011

Related U.S. Application Data

(60) Provisional application No. 61/355,859, filed on Jun. 17, 2010, provisional application No. 61/370,588, filed on Aug. 4, 2010.

(51) Int. Cl.
| | | |
|---|---|---|
| *A61K 49/00* | (2006.01) | |
| *A61B 5/00* | (2006.01) | |
| *G01N 33/94* | (2006.01) | |
| *G01N 33/68* | (2006.01) | |
| *G01N 21/64* | (2006.01) | |
| *A61B 5/08* | (2006.01) | |
| *A61B 5/145* | (2006.01) | |

(52) U.S. Cl.
CPC ............... *G01N 33/94* (2013.01); *A61B 5/411* (2013.01); *A61B 5/4211* (2013.01); *G01N 21/6486* (2013.01); *G01N 33/6893* (2013.01); *A61B 5/082* (2013.01); *A61B 5/14* (2013.01); *G01N 2800/06* (2013.01)

(58) Field of Classification Search
USPC .......................................... 424/9.1; 600/300
IPC .................................. A61K 49/00; A61B 5/00
See application file for complete search history.

(56) References Cited

PUBLICATIONS

Aswania et al. Relative Bioavailability of Sodium Cromoglycate to the Lung Following Inhalation, Using Uninary Excretion; British Journal of Clinical Pharmacology, vol. 47 (1999) pp. 613-618.*
Messerli et al. Cromolyn and Deep Inpiration-Induced Bronchoconstriction; Pneumonology, vol. 153 (1975) pp. 73-80.*

* cited by examiner

*Primary Examiner* — Kagnew H Gebreyesus
*Assistant Examiner* — Paul Martin
(74) *Attorney, Agent, or Firm* — Convergent Law Group LLP

(57) ABSTRACT

The invention provides a method of diagnosing entry of gastrointestinal contents into the respiratory tract of a patient suffering from reflux disease. The method comprises orally administering to a subject formulation comprising a detectable label that is not absorbed from the gastrointestinal tract but can be absorbed from the respiratory tract. The extent of the gastrointestinal contents entering the respiratory tract can be estimated by measuring the level of the detectable label in a body fluid, e.g., blood or urine.

23 Claims, No Drawings

DIAGNOSIS OF ENTRY OF GASTROINTESTINAL CONTENTS INTO RESPIRATORY TRACT OF HUMANS AND ANIMALS

FIELD OF THE INVENTION

The invention relates generally to the field of medical diagnoses and more particularly to methods and materials used for the detection of entry of gastrointestinal contents into the respiratory tract ("aspiration") in subjects (the subjects can be humans and non-human animals), with special attention to the diagnosis for the purpose of prevention and treatment of respiratory diseases.

BACKGROUND OF THE INVENTION

Gastro esophageal reflux disease (GERD) is a condition in which some of the stomach contents (solid and/or liquid) move backwards from the stomach into the esophagus (the tube from the mouth to the stomach). This action can irritate the esophagus, causing heartburn and other symptoms.

Gastroesophageal reflux disease (GERD), gastro-oesophageal reflux disease (GORD), gastric reflux disease, or acid reflux disease is defined as chronic symptoms or mucosal damage produced by the abnormal reflux of stomach acid to the esophagus. A typical symptom is heartburn.

This is commonly due to transient or permanent changes in the barrier between the esophagus and the stomach. This can be due to incompetence of the lower esophageal sphincter, transient lower esophageal sphincter relaxation, impaired expulsion of gastric reflux from the esophagus, or a hiatal hernia.

A different type of acid reflux which produces respiratory and laryngeal manifestations is laryngopharyngeal reflux (LPR), also called extraesophageal reflux disease (EERD). Unlike GERD, LPR is unlikely to produce heartburn, and is thus sometimes called silent reflux.

Useful investigations to diagnose GERD may include ambulatory Esophageal pH Monitoring, barium swallow X-rays, esophageal manometry, and Esophagogastroduodenoscopy (EGD).

The current gold standard for diagnosis of GERD is esophageal pH monitoring. It is the most objective test to diagnose the reflux disease and it also allows to monitor GERD patients in regards of their response to medical or surgical treatment. One practice for diagnosis of GERD is a short-term treatment with proton pump inhibitors, with improvement in symptoms suggesting a positive diagnosis. According to a systematic review, short-term treatment with proton pump inhibitors may help predict abnormal 24-hr pH monitoring results among patients with symptoms suggestive of GERD[7]. In this study, the positive likelihood ratio of a symptomatic response detecting GERD ranged from 1.63 to 1.87, with sensitivity of 0.78% though specificity was only 0.54%.

In general, an EGD is done when the patient either does not respond well to treatment or has alarm symptoms including dysphagia, anemia, blood in the stool (detected chemically), wheezing, weight loss, or voice changes. Some physicians advocate either once-in-a-lifetime or 5/10-yearly endoscopy for patients with longstanding GERD, to evaluate the possible presence of dysplasia or Barrett's esophagus, a precursor lesion for esophageal adenocarcinoma[8].

Esophagogastroduodenoscopy (EGD) (a form of endoscopy) involves insertion of a thin scope through the mouth and throat into the esophagus and stomach (often while the patient is sedated) in order to assess the internal surfaces of the esophagus, stomach, and duodenum.

The gastrointestinal contents may thus also enter the respiratory tract as a result of any condition that causes the backward movement of the gastrointestinal contents from the stomach to esophagus. The gastrointestinal contents contain many substances that are likely to be harmful to the respiratory tract: acid, digestive enzymes, microorganisms, allergens, proinflammatory substances and so on. There is increasing evidence that gastro esophageal reflux disease (GERD) is the underlying mechanism behind many disease conditions of the respiratory tract, such as infections and high morbidity in patients with lung transplants, asthma, bronchitis, pulmonary fibrosis and so on. At present, there are no acceptable methods to detect the entry of gastrointestinal (GI) contents into the respiratory tract.

SUMMARY OF THE INVENTION

Diagnostic formulations for use in diagnosing respiratory fluid in a patient suffering from gastro esophageal reflux disease (GERD) are disclosed. The concentration of the gastrointestinal contents entering the respiratory tract can be estimated by adding a detectable non-toxic label that is not absorbed from the gastrointestinal tract or from the respiratory tract. The label should be in a form that is biocompatible with the respiratory tract and the gastrointestinal tract. The label also should not be destroyed in the gastrointestinal or respiratory tract. If the contents of the gastrointestinal tract enters the respiratory tract, the respiratory fluid can be sampled (e.g., by bronchoscopy) and the concentration of the label in the respiratory tract can be measured, thus estimating the concentration of the gastrointestinal contents that entered the respiratory tract. For example, the diagnostic formulation may be comprised of an ingestible liquid; and a plurality of particles comprised of a biocompatible polymer such as carnauba wax and a non-radioactive label such as fluorescein.

Alternatively, a biocompatible label that is: (a) not destroyed in the gastrointestinal or respiratory tract; and (b) not absorbed from the gastrointestinal tract, but (c) is absorbed from the respiratory tract, can be used to estimate the amount of the gastrointestinal fluid that entered the respiratory tract. This is done by measuring the amount of the label that has entered the circulation (from the respiratory tract) by taking samples of blood or urine, and quantifying the amount of the label in those fluids. For example, cromolyn sodium is a harmless substance that is soluble in water, is not destroyed in the gastrointestinal tract or the respiratory tract, is not absorbed from the gastrointestinal tract but is absorbed from the respiratory tract. A water solution of cromolyn sodium can therefore be swallowed and the concentrations of cromolyn in blood and urine samples can be used to estimate the amount of gastrointestinal contents that entered the respiratory tract.

It is also possible to use two labels detectable in different ways in the same formulation, one such as cromolyn sodium, for estimating the amount of the gastrointestinal contents that entered the respiratory tract, and another label, such as fluorescein covered in carnauba wax, to estimate the concentration of gastrointestinal contents that entered the respiratory tract.

Both approaches can be also used purely for qualitative purposes to detect the entry of gastrointestinal contents into the respiratory tract. A label that is destroyed neither in the respiratory tract, nor in the gastrointestinal tract and which also has the properties of being absorbed from the respiratory tract but not from the gastrointestinal tract, can be used for qualitative detection of the entry of gastrointestinal contents into the respiratory tract. Such a label is swallowed and its presence is detected in the blood samples, or in urine if it is excreted via kidneys from blood to urine. Alternatively, a label that is not absorbed or destroyed in the gastrointestinal and respiratory tracts can be swallowed and subsequently detected in the respiratory fluid if the subject suffers from a condition that moves the contents of the gastrointestinal tract into the respiratory tract.

Although GERD is generally referred to here, those skilled in the art will understand that this invention is applicable to use in connection with any disorder that causes entry of gastrointestinal contents into the respiratory tract of the patient. Different subjects may be suffering from different disorders which result in involuntary aspiration of gastrointestinal contents. This may result in some of the gastrointestinal contents entering the respiratory tract of the patient causing damage. The present invention is intended to detect the presence of such gastrointestinal contents in the respiratory tract regardless of a particular disease or disorder which may have resulted in the presence of the gastrointestinal contents in the respiratory tract.

A method of diagnosing respiratory fluid in a patient suffering from gastro esophageal reflux disease (GERD) is disclosed. The method comprises (1) orally administering to a subject suspected of suffering from gastro esophageal reflux disease (GERD), a formulation comprised of a plurality of particles comprised of a biocompatible material (e.g. carnauba wax) and a detectable label (e.g. a fluorescent label), (2) allowing the formulation to remain in the subject over a period of time during which the subject would be expected to regurgitate formulation, (3) collecting respiratory fluid from the subject, and (4) analyzing the respiratory fluid to determine if the fluid contains the detectable label, and thereby determining if the subject aspirated gastrointestinal contents into the respiratory tract.

By carrying out the steps as described above it is possible to analyze the fluid collected from the respiratory tract and determine the concentration of the label in the respiratory fluid. The higher the concentration of the label in the respiratory fluid the greater the potential damage to the patient's respiratory tract due to involuntary aspiration of gastrointestinal contents.

In another embodiment of the invention, the formulation is also orally administered to the patient. However, instead of comprising particles with a fluorescent label (or other label) coated with carnauba wax (or other material) the formulation comprises a substance such as cromolyn sodium. Cromolyn sodium is water soluble and harmless. Further, cromolyn sodium is not absorbed in the gastrointestinal tract, but is absorbed in the respiratory tract. Those skilled in the art will recognize other compounds which have these characteristics. When the formulation is orally administered to the patient and there is aspiration of gastrointestinal contents into the respiratory tract, it is possible to test for the presence of the cromolyn in the patient's blood or urine. Thus, in accordance with this embodiment of the method the respiratory fluids of the patient do not need to be extracted. This method allows for the calculation of the total amount of gastrointestinal fluid which has entered the respiratory tract.

When a substance such as a cromolyn sodium is administered to the patient it may be advisable to first administer a control dose of cromolyn sodium orally to the patient in the morning. The dose is administered at a time when the patient would not be expected to experience any reflux. After administering the formulation such as cromolyn sodium the patient is not allowed to sleep or even lie down. Further, any steps that may need to be taken in order to avoid the patient experiencing reflux into the respiratory tract are taken. Blood and urine samples are then taken during the day and analyzed as a control. It may be that no cromolyn appears in the blood or urine. However, if a small amount appears, then that level of cromolyn can be used as a baseline to compare to the level when the formulation is administered and the patient is allowed to lie down, sleep and normally experience reflux into the respiratory tract. When the second administration occurs the same amount of cromolyn sodium is orally administered as was administered in the control. Carrying out a comparison will avoid false positives in the diagnosis of the subject, particularly in subjects that have abnormally high oral absorption of cromolyn. It is pointed out that in most "normal" subjects there will be substantially no absorption of cromolyn into the blood or urine unless the cromolyn is absorbed via the respiratory tract.

In yet another embodiment of the invention the two embodiments described above (coated particles and cromolyn sodium) are combined. Thus, the composition which is orally administered to the patient is a liquid formulation which includes the labeled particles coated with the biocompatible material such as carnauba wax and a material such as cromolyn sodium dissolved in the surrounding aqueous carrier. In accordance with this method follow-up analysis involves testing the respiratory fluid for the presence of the labeled particles to determine the concentration of the label in the fluid, and testing the blood and/or urine of the patient in order to calculate the total amount of gastrointestinal fluid which was aspirated into the respiratory tract.

The combination method described above can, of course, also be carried out using the control. The control is carried out as described above or the cromolyn sodium formulation is administered to the patient purely as a control and samples of the patient's blood and urine are taken during a period of time when the patient is not expected to experience reflux, such as during the day when the patient is not lying down or sleeping.

In still another embodiment of the invention the labeled material is coated with a composition which does not degrade inside the human body but which can be removed or degraded readily outside the human body by the application of heat or other chemicals. More specifically, the material coating the label does not melt at body temperature may be removed by the application of heat at a temperature above body temperature (>40° C.) or by the application of compound which readily dissolves the composition coating the label.

In yet another aspect of the invention positive controls can be used. For example, the patient can be administered a cromolyn formulation by inhalation. By knowing the precise amount of cromolyn administered into the patient's respiratory tract, and thereafter testing for cromolyn in the patient's blood and urine a comparison can be made to later tests when the cromolyn will be absorbed from reflux out of the patient's stomach into the respiratory tract. It is also, of course, possible to carry out both a negative and a positive control on the same patient.

The invention includes a method of diagnosing respiratory tract fluid in a patient by first orally administering to a subject a formulation comprised of a plurality of particles comprised of a biocompatible material and a detectable label. The formulation may include any number of particles, but for example 100, 500, 1,000 or more, 10,000 or more, 100,000 or more particles. The biocompatible material may be carnuba wax and the formulation may be an aqueous carrier which may be simply water. The label is preferably a non-toxic label such as a fluorescent label. The label may also be a radioactive label, a magnetic label and/or a UV labeled material. The formulation may also include a chromium salt. After administering the formulation the patient is allowed to rest during a period of time where aspiration of the formulation from the gastrointestinal tract into the respiratory tract would be expected to occur. After this time respiratory fluid is extracted from the patient such as by the use of bronchoscophy. The respiratory fluid collected from the patient is then analyzed in order to determine if the fluid contains the detectable label present within the formulation which was orally administered. The presence of the formulation label indicates that the patient is suffering from a disease such as GERD.

An aspect of the invention is that it is safe, and convenient for the patient.

Another aspect of the invention is that it is easily administered even in a primary healthcare setting, fast and cost-effective, with high specificity and selectivity.

Another aspect of the invention is that it avoids the use of radiolabels, because they are not practicable in a routine setting and multiple exposures to radioactivity raises safety concerns.

Another aspect of the invention is that to be able to estimate the concentration of the gastrointestinal contents that entered the respiratory tract, it is necessary to to avoid the use of labels that enter the blood circulation.

Another aspect of the invention is that it uses labels that stay as a tracer of the GI fluids that enter into the respiratory tract and remain intact in the GI and respiratory tracts.

Another aspect of the invention is that it uses materials presented in forms that are safe in the respiratory and GI tracts.

Another aspect of the invention is that it retains the label while in the body, presents the label readily when outside the body to a detector providing high specificity and selectivity (i.e., only the label material that was initially swallowed or otherwise placed into the GI tract and then enter the respiratory tract will be detected).

Another aspect of the invention is that the label used can be detected even if only minute quantities of the gastrointestinal materials entered the respiratory tract.

These and other objects, advantages, and features of the invention will become apparent to those persons skilled in the art upon reading the details of the methods and formulations as more fully described below.

DETAILED DESCRIPTION OF THE INVENTION

Before the present methods and formulations are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a particle" includes a plurality of such particles and reference to "the label" includes reference to one or more labels and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Fluorescein-Spray Drying

Prepare nuclei of <1 micron fluorescein particles by spray drying aqueous solutions of fluorescein. Then condense vapors of respiratory-tract compatible waxes such as carnauba was upon the fluorescein particles completely encapsulating the fluorescein. Make a suspension of these particles in water using usual pharmaceutical methods to stabilize these, add flavor etc. Patient swallows a precise amount of the liquid suspension prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. The fluorescent label is then released either as a result of the addition of a suitable solvent, or by increasing the temperature to dissolve the wax, or both.

The concentration of material in the respiratory tract entering due to reflux is estimated from the intensity of fluorescence using one of many detectors for fluorescence. The important parameter is the concentration of the fluorescent label per volume of the airway fluid in which it was contained as that is likely to be related to the harmful effects of the gastrointestinal fluid in the respiratory tract.

Example 2

Fluorescein—Flow Focusing

Prepare nuclei of <1 micron fluorescein particles by extruding a biocompatible wax (carnauba) in an outer tube and a fluorescein label in an inner tube in order to completely encapsulate the fluorescein. Details of the flow focusing method are described in U.S. Pat. No. 6,116,516 and related issued patents, all of which are incorporated herein by reference. Make a suspension of these particles in water using usual pharmaceutical methods to stabilize these, add flavor etc. Patient swallows a precise amount of the liquid suspension prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. The fluorescent label is then released either as a result of the addition of a suitable solvent, or by increasing the temperature to dissolve the wax, or both.

The concentration of material in the respiratory tract entering due to reflux is estimated from the intensity of fluorescence using one of many detectors for fluorescence. The important parameter is the concentration of the fluorescent label per volume of the airway fluid in which it was contained as that is likely to be related to the harmful effects of the gastrointestinal contents in the respiratory tract.

Example 3

Magnetic Particles-Flow Focusing

Magnetic particles may be suspended in a formulation and then swallowed for the diagnostic purposes described in this invention. However, it may be desirable to protect these particles from digestion in the gastrointestinal tract. Further, unencapsulated magnetic particles could be harmful to either the gastrointestinal tract, or the respiratory tract, or both. Using the flow focusing method it is possible to manufacture biocompatible encapsulated magnetic particles that are not digested in the gastrointestinal tract. Prepare nuclei of <1 micron magnetic particles by extruding a biocompatible wax (carnauba) in an outer tube and a magnetic particle label in an inner tube in order to completely encapsulate the magnetic particle. Make a suspension of these particles in water using usual pharmaceutical methods to stabilize these, add flavor etc. Patient swallows a precise amount of the liquid suspension prior to activity that is causing GIT reflux (e.g., prior to going to sleep).

The health care provider takes a sample of airway fluid through induced coughing, bronchoscopy, spontaneous coughing etc. The concentration of the gastrointestinal contents in the respiratory tract can be estimated by collecting with a magnet the magnetic particles and then counting them using one of the many methods available for such counting, or by measurement of the total magnetism. The sample may be also diluted in additional water, or a solvent that dissolves the wax. The magnetic particles can then be released either as a result of the addition of a suitable solvent, or by increasing the temperature to dissolve the wax, or both.

The important parameter is the concentration of the magnetic particle label per volume of the airway fluid in which it was contained as that is likely to be related to the harmful effects of the gastrointestinal fluid aspirated into the respiratory tract.

Example 4

UV Labeled Particles-Flow Focusing

Prepare nuclei of <1 micron UV labeled particles by extruding a biocompatible wax (carnauba) in an outer tube and a UV label or UV labeled particle in an inner tube in order to completely encapsulate the UV labeled particle. Make a suspension of these particles in water using usual pharmaceutical methods to stabilize these, add flavor etc. Patient swallows a precise amount of the liquid suspension prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. The UV labeled particle is then released either as a result of the addition of a suitable solvent, or by increasing the temperature to dissolve the wax, or both.

The amount of material in the respiratory tract entering due to reflux is estimated from the UV labeled particles detected using standard detectors. The important parameter is the concentration of the UV labeled particles per volume of the respiratory fluid in which it was contained as that is likely to be related to the harmful effects of the gastrointestinal fluid aspirated into the respiratory tract.

Example 5

Phosphorescent Particles-Flow Focusing

Prepare nuclei of <1 micron phosphorescent labeled particles by extruding a biocompatible wax (carnauba) in an outer tube and a phosphorescent labeled particle in an inner tube in order to completely encapsulate the phosphorescent labeled particle. Make a suspension of these particles in water using usual pharmaceutical methods to stabilize these, add flavor etc. Patient swallows a precise amount of the liquid suspension prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. The phosphorescent labeled particle is then released either as a result of the addition of a suitable solvent, or by increasing the temperature to dissolve the wax, or both.

The amount of material in the respiratory tract entering due to reflux is estimated from the phosphorescent labeled particles detected using standard detectors. The important parameter is the concentration of the phosphorescent labeled particles per volume of the airway fluid in which it was contained as that is likely to be related to the harmful effects of the gastrointestinal contents aspirated into the respiratory tract.

Example 6

Fluorescein—Flow Focusing With Cromolyn Sodium

Prepare nuclei of <1 micron fluorescein particles by extruding a biocompatible wax (carnauba) in an outer tube and a fluorescein label in an inner tube in order to completely encapsulate the fluorescein. Make a suspension of these particles in water using usual pharmaceutical methods to stabilize these, dissolve cromolyn sodium and add flavor etc. Patient swallows a precise amount of the liquid suspension including the dissolved cromolyn sodium prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. The fluorescent label is then released either as a result of the addition of a suitable solvent, or by increasing the temperature to dissolve the wax, or both.

Blood or urine samples are also taken and checked for cromolyn to estimate the total amount of gastrointestinal contents that entered the respiratory tract.

The concentration of material in the respiratory tract entering due to reflux is estimated from the intensity of fluorescence using one of many detectors for fluorescence. The important parameter is the concentration of the fluorescent label per volume of the airway fluid in which it was contained as that is likely to be related to the harmful effects of the gastrointestinal contents aspirated into the respiratory tract.

The amount of cromolyn in the blood or urine shows how much of the formulation of cromolyn swallowed did enter the respiratory tract because cromolyn will not enter the blood stream, or urine, via the GI tract.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of diagnosing abnormal entry of gastrointestinal contents into the respiratory tract in a subject, comprising:
   orally administering to a subject a first formulation comprising cromolyn contained therein when the subject would be expected to aspirate the formulation from the gastrointestinal tract into the respiratory tract;
   collecting a first body fluid following oral administration of the first formulation, wherein the body fluid is blood, urine or a respiratory fluid;
   analyzing a first body fluid to determine the level of cromolyn contained within the body fluid following oral administration of the first formulation;
   orally administering a negative control dose of a second formulation comprising cromolyn contained therein to the subject when the subject would not be expected to experience entry of gastrointestinal contents into the respiratory tract;
   collecting a second body fluid from the subject following the administration of the negative control dose, wherein the body fluid is blood or urine;
   analyzing the second body fluid following administration of the negative control dose to determine a baseline level of cromolyn in the subject;
   calculating an estimated total amount of gastrointestinal fluid which was aspirated into the respiratory tract following oral ingestion of the first formulation using the baseline level of cromolyn in the subject obtained after the administration of the negative control and the determined level of cromolyn contained within the first body fluid following administration of the first formulation when the subject would be expected to aspirate the formulation from the gastrointestinal tract into the respiratory tract; and
   diagnosing if the subject has an abnormal entry of gastrointestinal contents into the respiratory tract based on the estimated total amount of gastrointestinal fluid which was aspirated into the respiratory tract following oral ingestion of the first formulation.

2. The method of claim 1, wherein the formulation of the negative control dose is the same formulation as the formulation administered to diagnose abnormal entry of gastrointestinal contents into the respiratory tract of the subject.

3. The method of claim 1, wherein the first formulation is a liquid with cromolyn sodium dissolved therein.

4. The method of claim 1, wherein the first formulation comprises cromolyn in a liquid suspension.

5. The method of claim 1, wherein the second body fluid collected from the subject following the administration of the negative control dose is blood.

6. The method of claim 1, wherein the second body fluid collected from the subject following the administration of the negative control dose is urine.

7. The method of claim 1, wherein the first body fluid collected from the subject following the administration of the first formulation on the occasion when aspiration of gastrointestinal fluid in the respiratory tract is suspected is blood.

8. The method of claim 1, wherein the first body fluid collected from the subject following the administration of the first formulation on the occasion when aspiration of gastrointestinal fluid in the respiratory tract is suspected is urine.

9. The method of claim 1, wherein the cromolyn level detected in the blood following oral administration of the first formulation is used to calculate the estimated total amount of cromolyn absorbed via the respiratory tract.

10. The method of claim 1, wherein the same body fluid is analyzed following the administration of the first formulation and the administration of the negative control dose.

11. The method of claim 1, wherein the cromolyn level detected in the urine following oral administration of the first formulation is used to calculate the estimated total amount of cromolyn absorbed via the respiratory tract.

12. A method of diagnosing abnormal entry of gastrointestinal contents into the respiratory tract in a subject, comprising:
- orally administering to a subject a first formulation comprising cromolyn contained therein when the subject would be expected to aspirate the formulation from the gastrointestinal tract into the respiratory tract;
- obtaining a first body fluid following oral administration of the first formulation, wherein the body fluid is blood, urine or a respiratory fluid;
- analyzing a first body fluid to determine the level of cromolyn contained within the body fluid following oral administration of the first formulation;
- administering a positive control dose of a second formulation containing cromolyn to a subject by inhalation;
- detecting cromolyn levels in a second body fluid following administration of the positive control dose following inhalation of the second formulation, wherein the second body fluid is blood or urine;
- calculating an estimated total amount of gastrointestinal fluid which was aspirated into the respiratory tract following oral ingestion of the first formulation using the detected levels of cromolyn in the second body fluid following inhalation of the positive control dose and the analyzed levels of cromolyn in the first body fluid following oral ingestion of the first formulation when the subject would be expected to aspirate the formulation from the gastrointestinal tract into the respiratory tract; and
- diagnosing if the subject has an abnormal entry of gastrointestinal contents into the respiratory tract based on the estimated total amount of gastrointestinal fluid which was aspirated into the respiratory tract following oral ingestion of the first formulation by comparison to the results of the detected amount of cromolyn in the second body fluid using the control dose given by inhalation and the ingested first formulation.

13. The method of claim 12, wherein the formulation of the positive control dose administered by inhalation is the same formulation as the formulation administered by oral ingestion to diagnose abnormal entry of gastrointestinal contents into the respiratory tract in the subject.

14. The method of claim 12, wherein the first formulation comprises a cromolyn salt dissolved therein.

15. The method of claim 14, wherein the formulation of the positive control dose administered by inhalation is a different formulation from the formulation administered by oral ingestion to diagnose abnormal entry of gastrointestinal contents into the respiratory tract in the subject.

16. The method of claim 12, wherein the first formulation comprises cromolyn in a liquid suspension.

17. The method of claim 12, wherein the first formulation is a solid dosage form of cromolyn.

18. The method of claim 12, wherein the second body fluid collected from the subject following the administration of the positive control dose is blood.

19. The method of claim 12, wherein the second body fluid collected from the subject following the administration of the positive control dose is urine.

20. The method of claim 12, wherein the first body fluid collected is urine.

21. The method of claim 12, wherein the first body fluid collected is blood.

22. The method of claim 12, wherein the same body fluid is analyzed following the administration of the first formulation and the administration of the positive control dose.

23. The method of claim 12, wherein the first body fluid is urine.

* * * * *